United States Patent [19]

Mitchell

[11] 3,974,090
[45] Aug. 10, 1976

[54] IMINO ALKYLIMINO PHOSPHONATES AND METHOD FOR PREPARING AND USING SAME

[75] Inventor: Robert S. Mitchell, Webster Groves, Mo.

[73] Assignee: Monsanto Company, St. Louis, Mo.

[22] Filed: Mar. 20, 1975

[21] Appl. No.: 560,078

[52] U.S. Cl. ............................ 252/389 A; 252/181; 260/502.5; 21/2.7 A
[51] Int. Cl.² ........................................ C09K 15/18
[58] Field of Search ...................... 252/389 A, 181; 21/2.7 A; 260/502.5

[56] References Cited
UNITED STATES PATENTS

| | | | |
|---|---|---|---|
| 3,234,124 | 2/1966 | Irani | 210/38 |
| 3,288,846 | 11/1966 | Irani et al. | 260/500 |
| 3,336,221 | 8/1967 | Ralston | 210/58 |
| 3,476,799 | 11/1969 | Vogt et al. | 260/502.5 |
| 3,483,133 | 12/1969 | Hatch et al. | 252/389 |
| 3,630,938 | 12/1971 | Troscinski | 252/181 |
| 3,663,448 | 5/1972 | Ralston | 21/2.7 A |
| 3,837,803 | 9/1974 | Carter et al. | 252/389 A |

Primary Examiner—Leland A. Sebastian
Assistant Examiner—E. Suzanne Park
Attorney, Agent, or Firm—Thomas B. Leslie

[57] ABSTRACT

Imino ethylimino methyl phosphonates of the formula

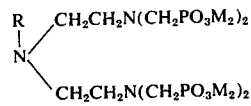

wherein R and M are hereinafter defined are prepared by reacting a phosphorus source (orthophosphorous acid or $PCl_3$ and $H_2O$), formaldehyde, and an amine of the formula

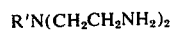

wherein R' is hereinafter defined. The compounds are useful as sequestrants for metal ions, as precipitation or scale inhibitors and as corrosion inhibitors in aqueous media.

30 Claims, No Drawings

IMINO ALKYLIMINO PHOSPHONATES AND METHOD FOR PREPARING AND USING SAME

BACKGROUND OF THE INVENTION

This invention relates to novel compounds useful as sequestrants and scale and corrosion inhibitors, methods of making such compounds, and methods of inhibiting scale formation and corrosion of metals therewith.

The utility of materials having the ability to sequester various ions from aqueous media is well recognized. For example, materials having ability to sequester calcium ions, iron ions, etc., are extensively utilized in treating water to prevent formation of scale or building up of precipitants in boilers, water towers, heat exchangers, etc. Some materials of this type are empirically found to also be useful as corrosion inhibitors. That is, they inhibit the corrosion of metals by water, and especially oxygen-bearing water.

The present invention has special utility in the prevention of the corrosion of metals which are in contact with circulating water, that is, water which is moving through condensers, engine jackets, cooling towers, evaporators or distribution systems, however, it can be used to prevent the corrosion of metal surfaces in other aqueous corrosive media. This invention is especially valuable in inhibiting the corrosion of ferrous metals including iron and steel (also galvanized steel) and nonferrous metals including copper and its alloys, aluminum and its alloys and brass. These metals are generally used in circulating water systems.

The major corrosive ingredients of aqueous cooling systems are primarily dissolved oxygen and inorganic salts, such as the carbonate, bicarbonate, chloride and/or sulfate salts of calcium, magnesium and/or sodium.

Most commercial water contains iron and alkaline earth metal cations, such as calcium, barium, magnesium, etc., and several anions such as hydroxide, bicarbonate, carbonate, sulfate, oxalate, phosphate, silicate fluoride, etc. When combinations of these anions and cations are present in concentrations which exceed the solubility of their reaction products under the conditions of the application (i.e., use), precipitates form until their reaction solubility product concentrations are no longer exceeded. For example, when the concentrations of calcium ion and sulfate ion exceed the solubility of the calcium sulfate, a solid phase of calcium sulfate will form.

Solubility product concentrations are exceeded for various reasons, among which are evaporation of the water phase, change in pH, pressure or temperature, and the introduction of additional ions which form insoluble compounds with the ions already present in the solution.

As these reaction products precipitate on the surfaces of the water-carrying system, they form scale. This adherent scale prevents effective heat transfer, interferes with fluid flow, facilitates corrosive processes, and harbors microorganisms. The presence of this scale is an expensive problem in many industrial water systems (e.g., boilers, cooling towers, evaporators, etc.), oilwells, and the like, causing delays and shutdowns for cleaning and removal.

Scale-forming compounds can be prevented from precipitating by inactivating their cations with chelating or sequestering agents, so that the solubility of their reaction products is not exceeded. Generally, this requires many times as much chelating or sequestering agent as cation, and these amounts under certain conditions are not always desirable or economical.

More than 25 years ago it was discovered that certain inorganic polyphosphates would prevent such precipitation when added in amounts less than the concentrations needed for sequestering or chelating. See, for example, Hatch and Rice, "Industrial Engineering Chemistry", vol. 31, pages 51 and 53; Reitmeier and Buehrer, "Journal of Physical Chemistry", vol. 44, No. 5, pages 535 and 536 (May 1940); Fink and Richardson U.S. Pat. No. 2,358,222; and Hatch U.S. Pat. No. 2,539,305, all of which are incorporated herein by reference. For sequestration, the mole ratio of precipitation inhibitor equivalents to scale forming cation is usually 1:1 or greater (2:1, 3:1, etc.). These ratios are referred to as stoichiometric. Substoichiometric amounts would include all mole ratios of precipitation inhibitor equivalent to scale forming cation that are less than the level required for sequestration; this phenomenon is known in the water treating art as the "threshold" effect.

It is to be understood that the term "threshold" as utilized herein refers to the chemical and/or physical phenomenon that less than stoichiometric quantities of the particular precipitation inhibitor can effectively prevent the precipitation of various metallic ions such as calcium, iron, copper and cobalt and/or alter those crystals formed such that the adherence to surfaces is substantially reduced. In other words, the threshold treatment of water is that technique by means of which less than stoichiometric quantities of the treating agent are added to interfere with the growth of crystal nuclei and thereby prevent the deposition of insoluble deposits.

Consequently, precipitation inhibitors which function as threshold agents as well as sequestering agents and corrosion inhibitors represent an advancement in the art and are in substantial demand.

SUMMARY OF THE INVENTION

It is an object of this invention to provide novel compounds useful as water treating agents.

Another object of this invention is to provide a method for manufacturing such compounds.

Another object of this invention is to provide methods for inhibiting the precipitation of metal ions from aqueous solution.

A still further object of this invention is to provide precipitation inhibitors which are effective as threshold scale inhibitors in aqueous solutions in less than stoichiometric amounts.

A further object of this invention is to provide new corrosion inhibiting methods, especially for metals in contact with aqueous corrosive media including cooling waters.

These and other objects will be better understood from the following detailed description.

The novel water treating compounds of the present invention contain multiple tertiary-substituted nitrogen atoms and multiple phosphonate groups. These compounds are imino ethylimino methyl phosphonates whose manufacture and utilities are more fully set forth in the description of preferred embodiments below.

DESCRIPTION OF PREFERRED EMBODIMENT

The novel compounds of this invention are represented by the formula

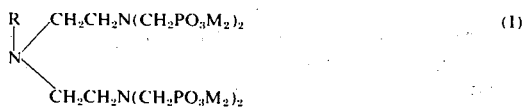

wherein R is $-CH_2PO_3M_2$ or $-CH_2CH_2N(CH_2PO_3M_2)_2$ and M is hydrogen, metal ions, ammonium ions, alkylammonium ions or mixtures thereof.

In the above formula M can be alike or unlike and is from the group metal ions and hydrogen or any cation which will yield sufficient solubility for the desired end use. The aforementioned metal ions are from the group of metals which includes, without limitation, alkali metals such as sodium, lithium and potassium; alkaline earth metals, such as calcium and magnesium; aluminum; zinc, cadmium; manganese; nickel, cobalt, cerium; lead; tin; iron; chromium; copper; gold; and mercury. Also included are ammonium ions and alkylammonium ions. In particular, those alkylammonium ions derived from amines having a low molecular weight, such as below about 300, and more particularly the alkyl amines, alkylene amines, and alkanol amines containing not more than two amine groups, such as ethyl amine, diethyl amine, propyl amine, propylene diamine, hexyl amine, 2-ethylhexylamine, N-butylethanol amine, triethanol amine, and the like are the preferred amines. It is to be understood that the preferred metal ions are those which render the compound a water-soluble salt in concentrations sufficient for the desired applications, such as the alkali metals, as well as the water-soluble salts from ammonium, alkylammonium and alkanol amine ions.

Exemlary compounds of the present invention include nitrilo tris[ethylimino bis(methyl phosphonic acid)], phosphonomethylimino bis[ethylimino bis(methyl phosphonic acid)] and the corresponding octa and hepta alkali metal, ammonium and alkylammonium salts of the acids such as octasodium, octaammonium and octamethylammonium nitrilo tris[ethylimino bis(methyl phosphonates)], heptapotassium, heptaammonium and heptaethylammonium phosphonomethylimino bis[ethylimino bis(methyl phosphonates)]; as well as mixed salts thereof such as dihydrogen hexasodium and trihydrogen pentaammonium nitrilo tris[ethylimino bis(methyl phosphonates)] and dihydrogen pentapotassium and trihydrogen tetraammonium phosphonomethylimino bis[ethylimino bis(methyl phosphonates)]. Other mixed salts or partial salts are likewise included in the above general formula.

In general, the compounds of the present invention are prepared by reacting together an (a) phosphorus source from the group orthophosphorous acid and a combination of $PCl_3$ and $H_2O$, (b) formaldehyde and (c) an amine of the formula

wherein R' is hydrogen or $-CH_2CH_2NH_2$.

It has been found that by forming a mixture of the above-described phosphorus source, formaldehyde and an amine of Formula II and subjecting the mixture to reaction conditions, compounds having multiple N—C—P linkages can be formed.

The amines falling within Formula II are described and prepared according to processes outlined in "Formaldehyde", J. F. Walker, published by Reinhold Publishing Company, New York (1964) pages 240-243 and in "Chemistry of Organic Cyanogen Compounds", V. Migrdichian, published by Reinhold Publishing Company, New York (1947) at pages 153-157, both of which are incorporated herein by reference. More specifically these amines can be prepared by the reaction of formaldehyde, ammonia and hydrogen cyanide by a stepwise reaction to produce the iminodiacetonitrile and nitrilotriacetonitrile and thereafter reducing the nitrile groups to amino groups by known procedures. For example, nitrilotriacetonitrile is produced by the above reaction and then reduced by hydrogenation to produce the desired amine, nitrilotriethyleneamine. It is understood that the amines falling within Formula II can be used in their (a) technical grade form, (b) chemically pure form, or (c) crude form which is obtained directly from the synthesis of the amine.

The formaldehyde reactant can be employed in any desired form, the more preferable being paraformaldehyde or formalin solutions.

For ease of description, orthophosphorous acid will generally be described hereinafter as the phosphorus source reactant. Orthophosphorous acid is available commercially.

It can be utilized in the processes of the present invention either as the acid, itself, or in the form of its salt, such as its mono- or diammonium salts, and mono- or dialkali metal salts. When orthophosphorous acid is utilized in the salt form, usually an amount of a supplementary acid sufficient to effectively convert the salt form into the more reactive orthophosphorous acid is used.

It is to be understood that while $H_3PO_3$ is used in this form, the individual ingredients $PCl_3$ and $H_2O$ which react to make $H_3PO_3$ can be used separately, e.g., added at different points of the process operation, or added simultaneously, i.e., two individual feed streams at the same time.

Ordinarily, for at least one from each of the reacting materials, i.e., items (a), (b) and (c) above, to undergo an interreaction to form one of the imino ethylimino methyl phosphonates they must simply be mixed together in certain relative proportions (described in more detail below), preferably in an acidic aqueous medium, and ordinarily subjected to an elevated temperature for a sufficient period of time to achieve the desired reaction. At room temperature, the rate of interreaction of these materials is slow, but where time is not a factor, the reaction can be carried out at 25°C. or lower. Increasing the temperature generally results in increasing the rate of the desired reaction, so that, usually, if the temperature of a mixture of phosphorous acid, amine of Formula II above, and formaldehyde is above about 70°C., the rate of their interreaction is sufficiently high so that conventional mixing and handling equipment can be utilized to produce the reaction product continuously and at a commercially practically cost, if desired. It has also been found that increasing the reaction temperature for the processes of this invention in the temperature range above about 75°C. up to 200°C. (the latter being the spontaneous decomposition temperature of orthophosphorous acid at atmospheric pressure) results in a fairly rapid increase in the rate of the desired reaction. Thus, for practical purposes, it is preferred that reaction temperature for the formation of the desired reaction product wherein orthophosphorous acid is utilized according to the processes of this invention, be above about 85°C. Temperatures within this preferred range, i.e., about 85°C to about 200°C., can readily be maintained by refluxing the aqueous reaction mixture at, above or below atmospheric pressure until the desired reaction has been completed.

It is believed surprising that the pH of the reaction medium has apparently an important influence upon the rate of the desired reaction. For example, it has been found that the rate of the desired reaction in mixtures containing the amine formaldehyde, and orthophosphorous acid in the molar ratio, respectively, of about 1:6:6 having a pH above about 4 is low. One possible reason for the low rate of the desired reaction in reaction media having pH's above about 4 is that apparently in such systems the competing oxidation of orthophosphorous acid to orthophosphoric acid takes precedence over the desired interreaction of orthophosphorous acid with formaldehyde and the amine. Actually, it is preferred that the pH of the reaction mixture of orthophosphorous acid plus formaldehyde plus amine, and usually at least some water, be below about 4 and preferably about 2 in order to achieve optimum results in the practice of the present invention. When one of the salts of orthophosphorous acid is utilized as a raw material, and when the ratio of reactive amine to orthophosphorous acid in the reaction mixture is relatively high, the "natural", or usual pH of the reaction mixture or reaction medium is generally not within the preferred range. However, the pH of the reaction medium can be adjusted into the most effective range by adding to the system any of the conventional acids having the ability to lower the pH of the reaction medium. For example, hydrochloric, sulfuric, hydrobromic, phosphoric, and sulfonic acids, as well as many others can be utilized for this purpose. Another example of providing a low pH and also a halide ion for a catalyst, hereinafter discussed, is the use of a halide salt and an acid. These two ingredients alone accomplish the desired result; however, they may react together to form a salt and a hydrogen halide which also achieves the end result. For example, the use of sodium chloride and sulfuric acid results in the formation of sodium bisulfate and hydrogen chloride.

Ordinarily the desired reaction will be fairly complete, under optimum reaction conditions in a resonable and practical period of time, for example, in less than about 3 hours, generally from about several minutes to about 3 hours, and fairly pure reaction products are produced.

While it is not essentially that water must be present in the reaction medium, it has been found that the presence of at least some water contributes substantially to such factors as keeping the reactants in solution, ease of handling of the reaction medium, ease of maintaining the desired reaction temperature by refluxing, ease of maintaining adequate heat transfer within the reaction mixture, decreasing the viscosity of the reaction products, etc. Thus, it is desirable that at least about 5 weight percent of water, based on the total weight of the raw reaction materials charged into the reaction mixture, and preferably at least about 15 weight percent of water be present in the reaction mixture before it has been exposed to temperatures above about 90°C. for any extended period of time. Additional water can also be added to the reaction medium from time to time if and as it is needed.

The processes of this invention can be carried out with conventional, readily available chemical processing equipment. For example, a conventional heated glass-lined mixing and reaction vessel fitted with a reflux condenser and a fairly efficient stirrer can be advantageously utilized in practicing any of the preferred embodiments of the invention described in the examples below.

The orthophosphorous acid, amine, and formaldehyde can be intermixed in several manipulative manners without detracting appreciably from the benefits that can be derived from the invention. For example, they can be simply poured together in the appropriate proportions, discussed below, into a mixing vessel, blended, and then heated to the reaction temperature. Or th ingredients can be warmed individually, before they are intermixed. The amine can be utilized per se or in the form of its salts such as the HCl salt form thereof. Sometimes it is convenient and desirable to intermix the amine with the phosphorous acid before they are heated very much above ambient temperatures.

Usually significantly better yields of the desired product, based on the amount of formaldehyde charged into the reaction vessel, can be attained if the formaldehyde is added slowly, e.g., over a period of from about 10 minutes to about 3 hours, to the mixture of orthophosphorous acid and amine while the temperature of said mixture is within the desired range.

The compounds of the present invention result from reacting (a) the phosphorus source, e.g., orthophosphorous acid and (b) formaldehyde with (c) the starting amine in a ratio of at least 5 to 6 moles, respectively, of (a) and (b) for each mole of (c) the starting amine, depending on whether such amine contains 5 or 6 amino hydrogen atoms. An excess of orthophosphorous acid from about 1 to 100% by weight can be utilized in such process. Excess formaldehyde can also be utilized to advantage. However, if the molar ratio of orthophosphorous acid and formaldehyde to the starting amine is raised above 5:5:1 or 6:6:1, respectively, resulting in an excess of formaldehyde or orthophosphorous acid, depending on the free amino hydrogen atoms in said amine, there may result side reaction products. Thus, for the production of relatively pure desired reaction products, it is preferred that the molar ratio of the starting amine to orthophosphorous acid in the reaction mixture be about 1:5 or 1:6, respectively, and that the molar ratio of the starting amine to formaldehyde in the reaction mixture be about 1:5 or 1:6, respectively, depending on the amino hydrogen content of said starting amine.

One reason why yields of the desirable products are generally not 100% of theory in the processes of this invention is that, in addition to the desired N—C—P linkage-forming reaction, the orthophosphorous acid also undergoes an oxidation reaction to form orthophosphoric acid under the conditions that usually favor the desired reaction. Since in most instances the presence of orthophosphoric acid in the final products is not particularly detrimental, the inclusion of excess orthophosphorous acid into the reaction medium is generally all that is necessary to make up for this "loss" of orthophosphorous acid from the desired reaction. However, it has been discovered that the presence of at least a catalytic amount of halide ions in the reaction mixture of amine, orthophosphorous acid, formaldehyde, and usually water inhibits the oxidation of orthophosphorous acid to orthophosphoric acid, and thus makes it possible to produce relatively more of the desired final product from a given reaction mixture than could otherwise be produced in the absence of halide ions therefrom. Apparently, any simple halide ion can be utilized to accomplish the inhibition described above, although for economic purposes chloride is preferred. The halide ion can apparently be introduced into the reaction mixture in any way whatever without detracting significantly from the benefits that can be derived from practicing the invention, provided it is introduced thereinto before the temperature of the reaction mixture has been heated to or held at about 70°C. for more than a few minutes. For example, it can be added in the form of a hydrohalide acid such as HCl, HBr, HI, etc., or as an inorganic salt, such as NaCl, KCl, NaBr, $CaCl_2$ and the like. Another convenient way is as the hydrogen chloride salt of the amine. As mentioned earlier, a mixture of a nonhalide containing acid and halide salt can be used to achieve the desired end result. Even very small amounts of halide ions in the reaction mixture have been found to inhibit the oxidation of orthophosphorous acid to some extent. Excellent results can be accomplished when there is utilized in the reaction mixture between about 0.01 and about 10, and preferably at least about 0.5 weight percent of halide ions. Halide ions in excess of these amounts can be present without any apparent detrimental effects on the processes of the invention. However, as a practical matter, generally, not more than about 20 weight percent of halide ions is utilized in the processes.

The acid and salt forms of the imino ethylimino methyl phosphonates falling within Formula I of the present invention have unique utility for treating water or aqueous systems and function as sequestering agents, as threshold agents and as corrosion inhibitors. It is to be understood that the term threshold as utilized herein refers to the chemical and/or physical phenomenon that less than stoichiometric quantities of the particular treating agent can effectively prevent the precipitation and/or alter the crystal forms of various salts of metallic ions such as calcium, iron, copper and cobalt. In other words, the threshold treatment of water is that technique by means of which less than stoichiometric quantities of the treating agent are added to interfere with the growth of crystal nuclei and thereby prevent the deposition of insoluble deposits.

The imino ethylimino methyl phosphonates of the present invention have utility for inhibition of the precipitation of metal ions from aqueous solutions, and/or alteration of those crystals formed such that the adherence to surfaces is substantially reduced. Typical applications also include liquid soaps and shampoos; bar soaps; scouring textiles, kier boiling; textile bleaching; metal cleaning compounds; rubber and plastics trace metal contamination (compounding and polymerization); pulp and paper trace metal contamination; saline water; oral compositions as anticalculus agents; photographic developers; hair bleaching and dyeing operations; stabilizing hydrogen peroxide solutions; brine solutions; brackish water; and squeeze treatment of producing oil wells.

The amount of the precipitation inhibitor necessary to be effective varies with, inter alia, the type and amount of problem metal ions, pH conditions, temperature and the like. When using substoichiometric or threshold treatment amounts, the preferred mole ratio of the precipitation inhibitor to the scale forming cation salt is from about 1:1.5 to about 1:10,000 with the concentration of precipitation inhibitor in the system being from about 0.1 to 500 ppm. When using sequestering amounts, i.e., at least stoichiometric quantities; the preferred mole ratio is from about 1:1 to 2.5:1.

The imino ethylimino methyl phosphonates of the present invention furthermore have utility for inhibiting corrosion of metal surfaces in contact with aqueous corrosive media, and particularly oxygen-bearing waters. It has been found that to effectively inhibit corrosion, at least 3 ppm, preferably from about 10 ppm to about 500 ppm. More preferably from about 10 to about 150 ppm of the imino ethylimino methyl phosphonate should be utilized in the corrosive medium. It is to be understood that greater than 500 ppm of these phosphonates can be used if desired so long as the higher amounts are not detrimental to the water system. Amounts as low as 1 ppm are found to be effective.

The corrosion inhibitors of the present invention are effective in both acidic or basic corrosive media. The pH can range from about 4 to about 12. For example, nitrilo tris[ethylimino bis(methyl phosphonic acid)], when used from about 3 to about 100 ppm is an effective corrosion inhibitor in a corrosive medium where the pH is from about 4 to about 12. In cooling towers the water system is generally maintained at a pH of from about 6.5 to 10.0, and most often at a pH of from about 6.5 to 8.5. In all such systems the inhibitors of the present invention are effective.

In addition to the utilization of the imino phosphonates of the present invention per se as corrosion inhibitors, it has been found that a cooperative effect exists in corrosion inhibition between these phosphonates and the zinc ion or chromates or dichromates. That is, the use of the imino phosphonates with the zinc ion or a chromate or dichromate more effectively inhibits corrosion than does an equal concentration of the imino phosphonate or the zinc or chromate alone. The zinc ion is preferably used in the same concentration as the imino phosphonate, e.g., a suitable corrosion inhibitor may consist of 50 ppm of zinc ion plus 50 ppm of an imino phosphonate. It is to be understood that the present invention also encompasses a corrosion inhibiting process and corrosion inhibition compositions utilizing mixtures of the imino phosphonates of this invention and a zinc-containing material, i.e., a zinc compound soluble in the corrosive media, which is capable of forming the zinc ion in an aqueous medium.

When a corrosion inhibiting composition is prepared from the two above materials there may conveniently be formed a dry composition thereof which may be later dissolved in water or fed directly to the aqueous system containing the metals to be protected. The maximum effect can be achieved by a composition of from about 20 to 90 percent by weight of the imino phosphonate and from about 10 to 80 percent by weight of a zinc compound soluble in the aqueous medium. Preferably such composition comprises from about 40 to about 80 percent by weight of the imino phosphonate and from about 20 to 60 percent by weight of the soluble zinc compound.

A combination of about 3 to 100 ppm of an imino phosphonate of this invention and about 2 to 100 ppm zinc ion will inhibit corrosion in most water systems.

The most preferred concentration range is from about 5 to 25 ppm of the imino phosphonate and about 5 to 25 ppm zinc ion. It is understood, however, that those concentrations are not limitative of the present invention.

The above-described cooperative effect is likewise realized with a chromate or dichromate, which may include any compound of hexavalent chromium soluble in the corrosive aqueous media, and preferably is an alkali metal or ammonium chromate or dichromate or chromic acid. Corrosion in most water systems can be inhibited by adding from 1 to 100 ppm of a imino phosphonate of this invention and from about 1 to about 100 ppm of a chromate or dichromate, preferably from about 5 to 25 ppm of a phosphonate and about 5 to 25 ppm chromate or dichromate. Larger or smaller amounts can be used if desired.

In corrosion inhibiting compositions the most effective compositions comprise mixtures of from about 1 percent to about 60 percent, and preferably from about 10 percent to about 40 percent of a water-soluble chromate or dichromate, based on the combined weights of the chromate or dichromate and the imino phosphonate of this invention.

It has also been found that compositions of imino phosphonates, zinc ion and chromate or dichromate are useful in inhibiting the corrosion of metal; that is all three components are cooperatively effective. The coaction of zinc and dichromates described in U.S Pat. No. 3,022,133, incorporated herein by reference, remains unaffected in the presence of the imino phosphonates of this invention.

Where the water systems are in contact with various metals such as steel and copper or copper-containing metals, it is frequently desirable to use, along with the imino phosphonate, either alone or in combination with zinc and/or chromium ions, a 1,2,3-triazole or a thiol of a thiazole, an oxazole or an imidazole such as are known in the art to inhibit the corrosion of copper. These azoles are likewise effective with the imino phosphonates of the present invention. The amounts of the azoles used depend on the particular aqueous systems. Generally concentrations of about 0.05 to 5 ppm thiol or triazole with about 3 to 100 ppm imino phosphonate and up to about 100 ppm zinc ion are satisfactory, preferably concentrations of from 0.5 to 2 ppm of the azole, about 5 to 25 ppm imino phosphonate and from about 5 to 25 ppm zinc ion.

It is within the scope of the present invention that the imino ethylimino methyl phosphonates of the present invention may also be used in aqueous systems which contain inorganic and/or organic materials (particularly, all ingredients or substances used by the water-treating industry), with the proviso that such materials do not render the imino phosphonates substantially ineffective for their end purpose.

These organic and inorganic materials include, without limitation, polycarboxylates, particularly those whose molecular weights are from about 2000 to about 20,000 and from about 20,000 to about 960,000; antifoam agents; water soluble polymers such as polyacrylic acid, polyacrylamide, partially hydrolyzed acrylamide and the like; tannins; lignins; deaerating materials; polymeric anhydrides (such as polymaleic anhydride); and sulfonated lignins. Other materials which can be used with said inhibitors include, for example, surface active agents, acetodiphosphonic acids, inorganic phosphates including orthophosphates, molecularly dehydrated phosphates and phosphonates, polyfunctional phosphated polyol esters, calcium and magnesium salts such as calcium or magnesium chlorides, sulfates, nitrates and bicarbonates and inorganic silicates. Furthermore, other scale and precipitation inhibitors such as amino tri(methylene phosphonic acid) may be used in combination with the inhibitors of the present invention. For examplary purposes only, these other precipitation inhibitors are described in U.S. Pat. Nos. 3,234,124; 3,336,221; 3,393,150; 3,400,078; 3,400,148; 3,434,969; 3,451,939; 3,462,365; 3,480,083; 3,591,513; 3,597,352 and 3,644,205, all of which publications are incorporated herein by reference. Other corrosion inhibitors can be used in combination with the imino phosphonates including those described in U.S. Pat. Nos. 3,483,133; 3,487,018; 3,518,203; 3,532,639; 3,580,855; and 3,592,764, all of which are incorporated herein by reference.

The following examples are included to illustrate the practice of the present invention and the advantages provided thereby but are not to be considered limiting. Unless otherwise specified, all parts are parts by weight and all temperatures are in degrees centigrade.

EXAMPLE I

Into a 500 milliliter flask equipped with a water condenser and dropping funnel are charged approximately 99 grams (0.6 mole) of 49.9% orthophosphorous acid (and which contained 9.4 grams of HCl) and 5.2 grams of 37% hydrochloric acid. The total moles of HCl is 0.4. The resultant mixture in the 500 milliliter flask is then heated by the addition thereto of approximately 14.6 grams (0.1 mole) of nitrilo triethyleneamine in its technical grade form. This amine is added over a period of approximately 10 minutes at the end of which time, the reaction mass has a temperature of about 75°C. The reaction mass is then heated for 20 minutes to bring it up to boiling thereby obtaining a homogeneous, clear solution having a boiling point of approximately 112°C.

The resultant clear solution in the flask is maintained at boiling, and over a period of approximately 2 hours, approximately 27 grams (0.66 mole) of paraformaldehyde is added. At the end of the 2 hour period, the reaction mixture, which is a clear solution, is held at boiling with reflux for an additional 30 minutes and then is cooled to 25°C. At 25°C., the solution is found to be clear with an amber color. One hundred forty-four grams of this solution is obtained with about 49% by weight thereof being the desired nitrilo tris phosphonic acid. Analysis of this solution by $p^{31}$ Nuclear Magnetic Resonance spectra (NMR) shows the presence of N—C—P linkage. After precipitation and reslurrying of a 50 gram portion of the solution and drying overnight there is obtained 24 grams of tan granular material. This material subjected to elemental analysis is identified as nitrilo tris[ethylimino bis(methyl phosphonic acid)], having the following structural formula:

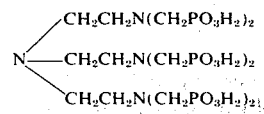

EXAMPLE II

Into a 500 milliliter flask equipped with a water condenser and dropping funnel are charged approximately 99 grams (0.6 mole) of 49.9% orthophosphorous acid (and which contained 9.4 grams of HCl) and 5.2 grams of 37% hydrochloric acid. The total moles of HCl is 0.4. The resultant mixture in the flask is then heated by the addition thereto of approximately 10.3 grams (0.1 mole) of imino diethyleneamine $HN(CH_2CH_2NH_2)_2$. This amine is added over a period of approximately 8–10 minutes at the end of which time, the reaction mass has a temperature of about 70–75°C. The reaction mass is then heated for about 20 minutes to bring it up to boiling thereby obtaining a homogeneous, clear solution having a boiling point of approximately 110–115°C.

The resultant clear solution in the flask is maintained at boiling, and over a period of approximately 2 hours, approximately 22 grams (0.66 mole) of paraformaldehyde is added. At the end of the 2 hour period, the reaction mixture, which is a clear solution, is held at boiling with reflux for an additional 30 minutes and then is cooled to about 25–30°C. At 25–30C. the solution is found to be clear with an amber color. This solution contains about 50% by weight thereof of the imino phosphonate which is analyzed, utilizing the $P^{31}$ Nuclear Magnetic Resonance spectra (NMR), which shows the presence of N—C—P linkage, and elemental analysis, as having the following structural formula:

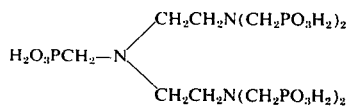

EXAMPLE III

The octasodium and octaammonium salts of the nitrilo tris[ethylimino bis(methyl phosphonic acid)] of Example I are prepared by neutralizing the acid in aqueous solution in 50 mls. of water with, respectively, a slight excess of sodium hydroxide and an excess of ammonium hydroxide solutions. The respective sodium and ammonium salts are recovered by conventional means. The ammonium salt is recovered by simply drying the ammonium salt solution to evaporate the water.

EXAMPLE IV

Using the same procedure as in Example III above the heptapotassium and heptamethylammonium salts of the phosphonomethylimino bis[ethylimino bis(methyl phosphonic acid)] of Example II are prepared.

EXAMPLE V

In order to demonstrate the utility of the imino methyl phosphonates, falling within Formula I above, the compounds of Examples I through IV are subjected to the sequestration procedure described in the book COORDINATION CHEMISTRY, "Calcium Complexing By Phosphorus Compounds", by C. F. Callis, A. F. Kerst and J. W. Lyons, pages 223–240, Plenum Press, 1969.

Approximately 1 gram of each of the above described compounds and which may be prepared via the procedure described in Examples I through IV, is individually and separately mixed with 0.1% by weight sodium oxalate in a 2-liter flask containing 100 milliliters of water. The pH in each case is adjusted by the addition of sodium hydroxide to a pH 11. Into each solution containing the separate and individual sequestration agents there is titrated a 0.1 molar calcium nitrate solution via the use of a Sargent-Malmstadt automatic titrator, Model SE, and which also measures the turbidity by light transmission. The amount of calcium nitrate solution added to each flask is sufficient to provide ample data to plot the point of inflection at which the sequestrant-containing solution goes from a relatively clear solution to a turbid one. This inflection point is then indicative of the amount of calcium that is sequestered by the particular sequestration agent.

The results of the sequestration test on the compounds of Examples I through IV show that the various imino phosphonic acids and salts are effective sequestrants for calcium which is one of the major undesirable cations in water which is used, for example, in cooling towers. Specifically, it is found that 100 grams of the above-described compound prepared in Example I, sequesters at least 1.5 grams of calcium. It is also found that the other compounds of Examples II, III and IV sequester calcium in the range of from about 0.3 grams to about 5.0 grams of calcium per 100 grams of the imino phosphonates.

Thus one of the unique applications of the compounds falling within Formula I is their use as a sequestration agent in treating aqueous systems containing calcium ions and which treatment would prevent the formation of calcium salts therein.

EXAMPLE VI

The imino phosphonates of the present invention falling within Formula I also exhibit threshold properties, i.e., they can be utilized in less than stoichiometric quantities to prevent the precipitation of salts of mineral acids, such as $CaCO_3$, in aqueous systems. Specifically, a test is conducted in which each of the compounds of Examples I and II is separately and independently mixed at 25°C. with 200 milliliters of water containing $NaHCO_3$. To the resultant mixture is added a concentrated $CaCl_2$ solution. The pH in each case is adjusted to 8.5 and maintained thereat with sufficient NaOH or HCl. The amounts of $CaCl_2$, $NaHCO_3$ and inhibiting agent used are sufficient to provide 1600 ppm of $CaCO_3$ and 10 ppm of the indicated imino phosphonate precipitation inhibitor. It is observed in each case that these less than stoichiometric quantities of said precipitation inhibitors or threshold agents effect a substantially clear solution for a period of at least 24 hours. Stating the results in a different manner, 10 parts per million of the indicated imino phosphonic acid threshold agent is effective in providing a substantially clear solution without precipitation which contains substantially greater than stoichiometric quantities of calcium carbonate therein. Analysis of aliquots of the solutions by titration of the sample solutions with a standard solution of ethylene diamine tetraacetic acid using an Eriochrome Black T indicator establishes that at least 94% of all the $CaCO_3$ present remains in solution.

EXAMPLE VII

An additional test of threshold inhibition of $CaSO_4$ by the imino phosphonic acid compounds of Examples I and II is conducted in generally the same manner as in Example VI above except that the test solutions contains 10,000 ppm of CaSO₄ as well as 10 ppm of the specific inhibitors at a pH of 7.0. It is again observed that these precipitation inhibitors or threshold agents maintain a substantially clear solution for a period of at least 24 hours. Analysis of samples of the solutions by the titration described above establishes that at least 95% of the CaSO₄ present remains in solution.

EXAMPLE VIII

Two solutions, A and B, are prepared in order to demonstrate the threshold effect of only 4 parts per million of nitrilo tris[ethylimino bis(methyl phosphonic acid)], the compound of Example I, in solutions containing large quantities of CaSO₄ and CaCO₃. The 4 ppm is based on a 100% active phosphonic acid basis. Solution A is prepared by dissolving the appropriate amount of said acid in water and then adding calcium chloride followed by the addition of sodium sulfate. The amounts of sodium sulfate and calcium chloride used are sufficient to result in the solution containing 10,000 ppm of CaSO₄ and then the pH is adjusted to 7. Solution B is prepared in the same manner except that there is used a CaCO₃ solution at a concentration of 1600 ppm. The solutions are stored with continuous agitation (NBS Gyrotory Shaker) at 25°C. Solutions A and B, both of which contain said imino phosphonic acid, remain clear over an extended period of at least 24 hours at the 10,000 ppm CaSO₄ level and at the 1600 ppm CaCO₃ level. About 96–100% of all the CaSO₄ and CaCO₃ remains in solution as further determined by titration of a sample of each solution with a standard solution of ethylene diamine tetraacetic acid using an Eriochrome Black T indicator, indicating that the imino phosphonic acid is a highly active threshold agent or precipitation inhibitor.

EXAMPLE IX

The effectiveness of the imino phosphonates of this invention as inhibitors of the corrosion of metals by oxygenated waters is shown by tests determining metallic corrosion rates. The tests are conducted in polarization test cells employing steel electrodes with synthetic hard municipal water at an initial pH of 7.0 and continuous aeration. The concentrations of the inhibitors is calculated on the basis of active acid form of the imino phosphonates and is carried out at two concentrations of 50 and 150 ppm of the synthetic water test medium. The rates of corrosion are determined by the Tafel Slope Extrapolation Method as described in "Handbook of Corrosion Testing and Evaluation" by Dean, France and Ketchum published by Wiley-Interscience, New York (1971), Chapter 8, from observed current densities and are expressed in terms of mils per year of metal loss.

The corrosion rates of a steel electrode at 35°C. in synthetic hard municipal water without inhibitor added and containing 50 to 150 ppm of nitrilo tris[ethylimino bis(methyl phosphonic acid)], the compound of Example I above, are determined as discussed above. The results are set out in Table I below.

TABLE I

| Test | Concentration of Corrosion Inhibitor(ppm) | Corrosion Rate (m.p.y.) |
|---|---|---|
| Control | None | 42 |
|  | 50 | 4 |

TABLE I-continued

| Test | Concentration of Corrosion Inhibitor(ppm) | Corrosion Rate (m.p.y.) |
|---|---|---|
|  | 150 | 5 |

EXAMPLE X

Additional tests are conducted in the same manner as Example IX above of the compounds of Examples II, III and IV above at the same concentrations of active imino phosphonate inhibitor. The results utilizing these inhibitor compounds are similar to those obtained in Example IX in that the rates of corrosion range from about 4 to 10 mils per year in the same corrosive aerated water medium.

The foregoing examples have been described in the specification for the purpose of illustration and not limitation. The present invention may be otherwise embodied and practiced within the scope of the following claims.

What is claimed is:

1. A nitrilo tris[ethylimino bis(methyl phosphonic acid)] compound having the general formula

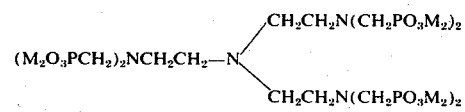

wherein M is selected from the group consisting of hydrogen, alkali metal ions, ammonium ions, alkylammonium ions and mixtures of hydrogen and at least one other of said ions.

2. The compound of claim 1 wherein each M is sodium.

3. The compound of claim 1 wherein each M is an alkali metal ion.

4. The compound of claim 1 wherein each M is an ammonium ion.

5. The compound of claim 1 wherein each M is an alkylammonium ion.

6. Nitrilo tris[ethylimino bis(methyl phosphonic acid)].

7. Octasodium nitrilo tris[ethylimino bis(methyl phosphonate)].

8. Octaammonium nitrilo tris[ethylimino bis(methyl phosphonate)].

9. A process for preparing a nitrilo tris[ethylimino bis(methyl phosphonic acid)] which comprises forming an aqueous mixture having a pH below about 4 and containing (1) a phosphorus source selected from the group consisting of (a) orthophosphorous acid and (b) a combination of PCl₃ and H₂O, (2) formaldehyde and (3) nitrilotriethyleneamine in a molar ratio of (1) to (2) to (3) of about 6:6:1, and subjecting said mixture to temperatures above about 70°C. whereby said nitrilo tris[ethylimino bis(methyl phosphonic acid)] having multiple N—C—P linkages is formed.

10. The process of claim 9 wherein said mixture additionally contains about 0.01 weight percent to about 10 weight percent of halide ions in order to inhibit the oxidation of said orthophosphorous acid to orthophosphoric acid during said process.

11. A process for preparing nitrilo tris[ethylimino bis(methyl phosphonic acid)] which process comprises forming an aqueous mixture of nitrilotriethyleneamine and orthophosphorous acid in a molar ratio of said amine to said acid of about 1:6, and at least about 0.5 weight percent of halide ions, the pH of said mixture being below about 4, and blending into said mixture over a period of from about 10 minutes to about 3 hours while said mixture is at a temperature above about 85°C. at least under 6 molar equivalents of formaldehyde, based on the amount of said amine in said mixture, whereby said nitrilo tris[ethylimino bis(-methyl phosphonic acid)] is produced.

12. A method of inhibiting the precipitation of scale-forming salts in an aqueous system comprising adding to said system at least a precipitation inhibiting amount of a nitrilo tris[ethylimino bis(methyl phosphonic acid)] compound having the general formula

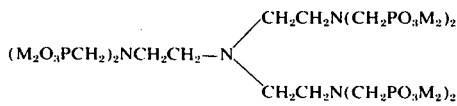

wherein M is selected from the group consisting of hydrogen, alkali metal ions, ammonium ions, alkylammonium ions and mixtures of hydrogen and at least one other of said ions.

13. The method of claim 12 wherein the scale-forming salt is an alkaline earth metal carbonate, sulfate or oxalate.

14. The method of claim 12 wherein the mole ratio of precipitation inhibitor to scale-forming salts is from about 1:1.5 to about 1:10,000.

15. The method of claim 14 wherein the precipitation inhibitor is present in the system at concentrations from about 0.1 to about 500 parts per million.

16. The method of claim 12 wherein each M is sodium.

17. The method of claim 12 wherein each M is an alkali metal ion.

18. The method of claim 12 wherein each M is an ammonium ion.

19. The method of claim 12 wherein said compound is nitrilo tris[ethylimino bis(methyl phosphonic acid)].

20. A method of inhibiting the corrosion of metals in a water system comprising maintaining in the water of said system at least 3 parts per million of a nitrilo tris[ethylimino bis(methyl phosphonic acid)] compound having the general formula

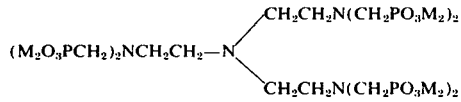

wherein M is selected from the group consisting of hydrogen, alkali metal ions, ammonium ions, alkylammonium ions and mixtures of hydrogen and at least one other of said ions.

21. The method of claim 20 wherein each M is sodium.

22. The method of claim 20 wherein each M is an alkali metal ion.

23. The method of claim 20 wherein each M is an ammonium ion.

24. The method of claim 20 wherein the water of said system additionally contains a water-soluble compound of hexavalent chromium.

25. The method of claim 20 wherein the water of said system additionally contains a zinc compound soluble in water in the presence of said phosphonic acid compound.

26. The method of claim 20 wherein the water of said system additionally contains from about 0.05 to 5 ppm of a compound selected from the group consisting of 1,2,3-triazoles, thiols of thiazoles, thiols of oxazoles, thiols of imidazoles and mixtures thereof.

27. The method of claim 26 wherein the water of said system additionally contains a zinc compound soluble in water in the presence of said phosphonic acid compound, sufficient to supply to said water from about 2 to 100 ppm of zinc ions.

28. The method of claim 20 wherein the said compound is nitrilo tris[ethylimino bis(methyl phosphonic acid)].

29. A composition useful in inhibiting the corrosion of metals in a water system consisting essentially of from about 20 percent to about 90 percent by weight of a nitrilo tris[ethylimino bis(methyl phosphonic acid)] compound having the general formula

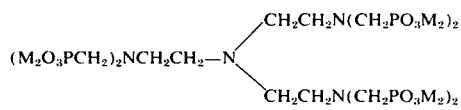

wherein M is selected from the group consisting of hydrogen, alkali metal ions, ammonium ions, alkylammonium ions and mixtures of hydrogen and at least one other of such ions, and from about 10 percent to about 80 percent of a zinc compound soluble in water in the presence of said phosphonic acid compound.

30. A composition useful in inhibiting the corrosion of metals in a water system consisting essentially of (1) from about 20 percent to about 90 percent by weight of a nitrilo tris[ethylimino bis(methyl phosphonic acid)] compound having the general formula

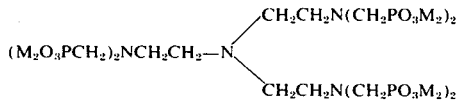

wherein M is selected from the group consisting of hydrogen, alkali metal ions, ammonium ions and mixtures of hydrogen and at least one other of such ions, (2) from about 1 percent to about 10 percent by weight of a compound selected from the group consisting of 1,2,3-triazoles, thiols of thiazoles, thiols of oxazoles, thiols of imidazoles and mixtures thereof, and (3) up to about 79 percent by weight of a zinc compound soluble in water in the presence of said phosphonic acid compound.

* * * * *

UNITED STATES PATENT OFFICE
CERTIFICATE OF CORRECTION

PATENT NO. : 3,974,090
DATED : August 10, 1976
INVENTOR(S) : Robert S. Mitchell

It is certified that error appears in the above–identified patent and that said Letters Patent are hereby corrected as shown below:

Column 4, line 32 " salt, such as its mono- or diammonium salts, and mono-" should read --- salts, such as its mono- or diammonium salts, and mono- ---.

Column 5, line 55, "While it is not essentially that water must be present" should read --- While it is not essential that water must be present ---.

Column 16, Claim 30, line 8, after "ammonium ions" should appear --- , alkylammonium ions ---.

Signed and Sealed this

Twenty-third Day of November 1976

[SEAL]

Attest:

RUTH C. MASON
Attesting Officer

C. MARSHALL DANN
Commissioner of Patents and Trademarks